(12) United States Patent
Yang et al.

(10) Patent No.: US 7,238,677 B2
(45) Date of Patent: Jul. 3, 2007

(54) PREVENTION OF UROGENITAL INFECTIONS

(75) Inventors: Shu-Ping Yang, Alpharetta, GA (US); Yanbin Huang, Roswell, GA (US); Ilona F. Weart, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/401,522

(22) Filed: Mar. 28, 2003

(65) Prior Publication Data

US 2004/0192642 A1    Sep. 30, 2004

(51) Int. Cl.
    *A61K 31/70*    (2006.01)
(52) U.S. Cl. .................................................. 514/54
(58) Field of Classification Search ............... 514/54; 536/55.1, 55.2, 123, 123.1
    See application file for complete search history.

(56) References Cited

U.S. PATENT DOCUMENTS

| | | | |
|---|---|---|---|
| 4,051,842 A | 10/1977 | Hazel et al. ............. 128/2.06 E |
| 4,140,122 A | 2/1979 | Kuhl et al. ................ 128/260 |
| 4,141,973 A | 2/1979 | Balazs | |
| 4,383,529 A | 5/1983 | Webster ....................... 604/20 |
| 4,615,697 A | 10/1986 | Robinson .................... 604/890 |
| 4,665,060 A | 5/1987 | Mardh et al. ................. 514/61 |
| 4,725,585 A | 2/1988 | Wenge et al. ................ 514/54 |
| 4,746,504 A | 5/1988 | Nimrod et al. ............. 424/1.73 |
| 4,762,824 A | 8/1988 | Kallenius et al. ............ 514/54 |
| 4,784,991 A | 11/1988 | Nimrod et al. ............... 514/62 |
| 4,851,521 A | 7/1989 | Della Valle et al. ....... 536/55.1 |
| 4,855,128 A | 8/1989 | Lynch et al. ................ 424/49 |
| 5,002,759 A | 3/1991 | Gaffar et al. ................ 424/49 |
| 5,401,723 A | 3/1995 | Gaffar et al. ................ 514/21 |
| 5,409,902 A | 4/1995 | Carson et al. ............... 514/23 |
| 5,514,665 A | 5/1996 | Speert et al. ................ 514/53 |
| 5,591,724 A * | 1/1997 | Morales et al. .............. 514/54 |
| 5,604,200 A | 2/1997 | Taylor-McCord ............. 514/8 |
| 5,650,432 A | 7/1997 | Walker et al. ............. 514/456 |
| 5,700,458 A | 12/1997 | Mandeville, III et al. .................... 424/78.07 |
| 5,795,958 A | 8/1998 | Rao et al. ................... 530/331 |
| 5,840,322 A | 11/1998 | Weiss et al. ................ 424/405 |
| 5,883,079 A | 3/1999 | Zopf et al. ................... 514/25 |
| 6,051,701 A | 4/2000 | Cialdi et al. ................ 536/123 |
| 6,063,773 A | 5/2000 | Anderson et al. ............. 514/57 |
| 6,224,857 B1 | 5/2001 | Romeo et al. | |
| 6,290,959 B1 | 9/2001 | Wu et al. .................. 424/150.1 |
| 6,375,963 B1 | 4/2002 | Repka et al. ................ 424/402 |
| 6,417,173 B1 | 7/2002 | Roufa et al. ................. 514/54 |
| 2003/0204180 A1 | 10/2003 | Huang et al. ............ 604/890.1 |
| 2005/0095219 A1 | 5/2005 | Yang et al. | |

FOREIGN PATENT DOCUMENTS

| DE | 19813234 A1 | 9/1999 |
|---|---|---|
| EP | 0656215 A1 | 6/1995 |
| EP | 0769298 A2 | 4/1997 |
| EP | 0962202 A1 | 12/1999 |
| EP | 1275395 A2 | 1/2003 |
| JP | 09-208476 | 8/1997 |
| JP | 2002238995 A | 8/2002 |
| WO | WO-9417840 A1 | 8/1994 |
| WO | WO-9603973 A1 | 2/1996 |
| WO | WO-00/45804 | 8/2000 |
| WO | WO-02/24223 | 3/2002 |
| WO | WO-04093887 A1 | 11/2004 |

OTHER PUBLICATIONS

An, Yuehuei H., et al., "Concise review of mechanisms of bacterial adhesion to biomaterial surfaces", *Journal of Biomedical Materials Research*, 43(3), (Fall 1998),338-348.

Chaffin, W L., et al., "Cell wall and secreted proteins of *Candida albicans*: identification, function, and expression", *Microbiology & Molecular Biology Reviews*, 62(1), (Mar. 1998), 130-80.

Cho, S Y., et al., "Opportunistic fungal infection among cancer patients", *American Journal of Clinical Pathology*, 72(4), (Oct. 1979),617-21.

Connell, H , et al., "Fimbriae-mediated adherence induces mucosal inflammation and bacterial clearance", *In: Toward anti-adhesion therapy for microbial diseases by Itzhak Kahane ; Itzhak Ofek*, New York : Plenum Press,(1996),73-80.

Cunningham, M W., "Pathogenesis of group A streptococcal infections", *Clinical Microbiology Reviews*, 13(3), (Jul. 2000),470-511.

Goodison, S , et al., "CD44 cell adhesion molecules", *Molecular Pathology*, 52(4), (Aug. 1999),189-96.

Hardingham, Timothy E., et al., "Aggrecan, the Chondroitin Sulfate/Keratan Sulfate Proteoglycan from Cartilage", *In: Articular Cartilage and Osteoarthritis*, edited by Klaus E. Kuetner et al., New York : Raven Press,(1992),5-20.

Hardingham, Timothy E., et al., "BBA Report. The specific interaction of hyaluronic acid with cartilage proteoglycans", *Biochimica et Biophysica Acta*, 279, (1972),401-405.

Hardingham, Timothy E., et al., "Hyaluronic Acid in Cartilage and Proteoglycan Aggregation", *Biochemical Journal*, 139(3), (Jun. 1974),565-581.

Hardingham, Timothy E., "The role of link-protein in the structure of cartilage proteoglycan aggregates", *Biochemical Journal*, 177(1), (Jan. 1, 1979),237-247.

Heinegard, Dick , et al., "Aggregation of cartilage proteoglycans. 3. Characteristics of the proteins isolated from trypsin digests of aggregates", *Journal of Biological Chemistry*, 249(13), (Jul. 10, 1974),4250-4256.

(Continued)

*Primary Examiner*—Elli Peselev
(74) *Attorney, Agent, or Firm*—Schwegman, Lundberg, Woessner & Kluth, P.A.

(57) ABSTRACT

The invention provides hyaluronic acid compounds and derivatives thereof for preventing urogenital infections by a variety of pathogens, as well as compositions, articles and methods for treating and preventing urogenital infections.

12 Claims, 3 Drawing Sheets

OTHER PUBLICATIONS

Hornef, M W., et al., "Bacterial strategies for overcoming host innate and adaptive immune responses", *Nature Immunology*, 3(11), (Nov. 2002),1033-40.

Hultgren, S J., et al., "Bacterial adhesins and their assembly", *In: Escherichia coli and Salmonella : cellular and molecular biology/ Frederick C Neidhardt; Roy Curtiss*, Washington, D.C. : ASM Press,(1996),2730-2756.

Kahane, Itzhak , et al., "Toward anti-adhesion therapy for microbial diseases", *New York : Plenum Press*, Fimbriae-Mediated Adherence Induces Mucosal Inflammation and Bacterial Clearance: Consequences for Anti-Adhesion Therapy by H. Connell et al,(1996),73-80.

Klotz, S. A., "Adherence of Candida Albicans to Components of the Subendothelial Extracellular Matrix", *FEMS Microbiology Letters*, 68 (3), Elsevier Science Publishers, Amsterdam, NL,(Mar. 15, 1990),249-253.

Luo, et al., "Modification of Natural Polymers: Hyaluronic Acid", *In: Methods in Tissue Engineering; Anthony Atala; R P Lanza (eds.)*, San Diego, CA :; Academic Press,(2001),539-553.

Mobastery, S , et al., "Bacterial antibiotic resistance", *In: Encyclopedia of life sciences/Nature Publishing Company*, London ; New York : Nature Pub. Group,(2002).

Muhldorfer, I , et al., "*Escherichia coli* in urinary tract infections", *In: Molecular medical microbiology / Max Sussman*, San Diego : Academic Press,(2002),1515-1540.

Ofek, I , "Adhesins as lectins: specificity and role in infection", *Current Topics in Microbiology & Immunology*, 151, (1990),91-113.

Petrin, D , et al., "Clinical and microbiological aspects of Trichomonas vaginalis", *Clinical Microbiology Reviews*, 11(2): (Apr. 1998),300-17.

Reid, G , "Probiotics for urogenital health", *Nutrition in Clinical Care*, 5(1), (Jan.-Feb. 2002),3-8.

Schoor, Richard A., et al., "Secretory IgA differentially promotes adherence of type 1-piliated *Escherichia coli* to immortalized vaginal epithelial cell lines", *Urology*, 57(3), (Mar. 2001),556-561.

Sharon, N , "Bacterial lectins, cell-cell recognition and infectious disease", *FEBS Letters*, 217(2), (Jun. 15, 1987),145-57.

Shnayerson, M , "The killer bug", *Fortune (Industrial Edition)*, 146(6), (2002),149-156.

Varki, A , "Biological roles of oligosaccharides: all of the theories are correct", *Glycobiology*, 3(2), (Apr. 1993),97-130.

Walsh, C , "Molecular mechanisms that confer antibacterial drug resistance", *Nature*, 406(6797), (Aug. 17, 2000),775-81.

Zopf, D , et al., "Oligosaccharide anti-infective agents", *Lancet*, 347(9007), (Apr. 13, 1996),1017-21.

Alho, Anna M., et al., "The Hyaluronate Receptor Is Preferentially Expressed on Proliferating Epithelial Cells", *The Journal of Cell Biology*, 108, (1989), 1557-1565.

Laurent, C., et al., "Localization and quantity of hyaluronan in urogenital organs of male and female rats", *Cell Tissue Research*, 279, (1995), 241-248.

Lee, Janet Y., et al., "Hyaluronan: a multifunctional, megaDalton, stealth molecule", *Current Opinion in Cell Biology*, 12, (2000), 581-586.

Lesley, Jayne, et al., "Hyaluronan Binding by Cell Surface CD44", *The Journal of Biological Chemistry*, 275, (Sep. 2000), 26967-26575.

Mammen, Mathai, et al., "Polyvalent Interactions in Biological Systems: Implications for Design and Use of Multivalent Ligands and Inhibitors", *Angewandte Chemie International Ed.*, 37 (1998), 2754-2794.

Okada, M., "Molecular design and syntheses of glycopolymers", *Progress in Polymer Science*, 26, (2001), 67-104.

Sackmann, Erich, et al., "Cell Adhesion as Wetting Transition?", *Chemphyschem*, 3, (2002), 262-269.

Simon, P. M., et al., "Inhibition of Helicobacter pylori Binding to Gastrointestinal Epithelial Cells by Sialic Acid-Containing Oligosaccharides", *Infection and Immunity*, 65(2), (Feb. 1997), 750-757.

Yoshizumi, Akira, et al., "Self-Assembled Monolayer of Sugar-Carrying Polymer Chain: Sugar Balls from 2-Methacryloyloxyethyl D-Glucopyranoside", *Langmuir*, 15, (1999), 482-488.

Vasilionkaitis, V., "Search for an Artificial Lubricant for Joints Based on Complexes of Poly(Vinyl Chloride) with Hyaluronic Acid Biopolymers", *Nauchno-Issled. Inst. Eksp. Klin. Med., Vilnius, USSR sint. Izuch. Fiziol. Akt. Veshchestv, Tezisy Dokl. Mezhvuz Nauchn. Konf. Uchasteim Farmakol.Latv. Est. SSR, 20-1. Vil'nyus. Gos. Univ. Vilnius USSR* (1975) (Abstract only).

Vasilionkaitis, V., "Search for an Artificial Lubricant for Joints Based on Complexes of Poly(Vinyl Chloride) with Hyaluronic Acid Biopolymers", *Nauchno-Issled. Inst. Eksp. Klin. Med., Vilnius, USSR sint. Izuch. Fiziol. Akt. Veshchestv, Tezisy Dokl. Mezhvuz Nauchn. Konf. Uchasteim Farmakol.Latv. Est. SSR, 20-1. Vil'nyus. Gos. Univ. Vilnius USSR* (1975) (Abstract only).

Ramires, P. A., et al., "Biocompatibility of Poly(vinyl alcohol)-Hyaluronic Acid and Poly(vinyl alcohol)-gellan Membranes Crosslinked by Glutaraldehyde Vapors", *Journal of Materials Science: Materials in Medicine*, 13, (Jan. 2002),119-123.

* cited by examiner

PREVENTION OF UROGENITAL INFECTIONS

FIELD OF THE INVENTION

The invention relates to the use of compositions containing hyaluronic acid compounds to prevent attachment of pathogens to vaginal tissues.

BACKGROUND OF THE INVENTION

The vagina is fairly resistant to infection due to its marked acidity, balanced ecosystem and thick protective epithelium. However, numerous insults can affect the vaginal defense system and lead to increased susceptibility to vaginal infection. For example, low estrogen levels in menopausal and hypogonadal women can affect the thickness of the vaginal epithelium. Antibiotics can alter the microbiology of the vagina. Semen during intercourse and blood during menstruation can increase vaginal pH. Stress, fatigue, chronic diseases such as diabetics and human immunodeficiency disease (HIV) affect not only the immune system but also the pH of the vagina. These factors can breakdown the balanced microenviroment in the vagina and increase the risk of vaginal infection by a variety of organisms.

Vaginal colonization of the vagina by pathogenic bacteria such as *Escherichia coli* is a significant step in ascending urinary tract infections (UTIs), which affect about 10–20% of women at some time in their life and which cost $5 billion per year in healthcare costs. Estrogen-depleted post-menopausal women are the highest risk group for acquiring urinary tract infections due to the thinning of the vaginal mucosa and the increased pH of the vaginal environment in these women. Recurrences of both vaginal and urinary tract infections are frequent following the initial episode. Hence, prevention of the initial infection is important for avoiding repeated urogenital infections.

Without treatment, vaginal infections can increase the risk of sexually transmitted diseases and induce complications such as urinary tract infections, pelvic inflammatory diseases and pre-term births. Currently, the control of such infections relies heavily on using antibiotics. However, extensive use of antibiotics for prevention of infection can be detrimental, not only because of the increased risk of generating antibiotic-resistant microorganisms, but also because indiscriminate killing of beneficial bacteria in urogenital tract can leave it susceptible to infection by other pathogens. Hence, there is increasing concern that compositions containing antibiotics should not be used routinely for treating urogenital infections.

Thus, a need exists for compositions and methods for preventing urogenital infections without the use of antibiotics or harsh chemicals that can upset the natural balance within the urogenital tract.

SUMMARY OF THE INVENTION

The present invention is directed to compositions and methods for treating and inhibiting infections within the urogenital tract, for example, within the vagina and urinary tract. In some embodiments, the invention is directed to a composition comprising an effective amount of hyaluronic acid and a pharmaceutically acceptable excipient for use in the urogenital area, wherein the composition can inhibit adherence of *Escherichia coli* or *Candida albicans* to mammalian epithelial cells.

The invention is also directed to a method for treating a urogenital infection in a mammal comprising administering to the mammal's urogenital tract an effective amount of hyaluronic acid and a pharmaceutically acceptable excipient for use in the urogenital area, wherein the composition can inhibit adherence of *Escherichia coli* or *Candida albicans* to mammalian epithelial cells.

In some embodiments, the structure of the hyaluronic acid compound is generally that of formula I:

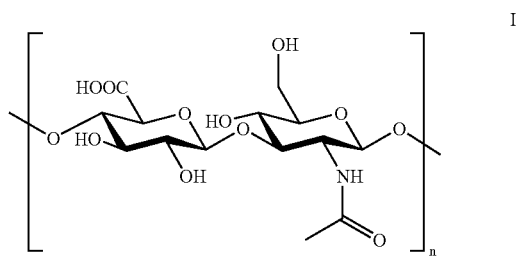

wherein n is an integer of about 2 to about 100,000. The value of n can vary.

Moreover, in many embodiments some of the individual sugar units of the hyaluronic acid can have a variety of substituents in place of the hydroxy (—OH), carboxylate (—COO$^-$), and methylenehydroxy (—CH$_2$—OH) substituents that are often found in hyaluronic acid preparations. In general, the exact type of hyaluronic acid compound(s), as well as the size of the compound can vary to achieve optimal coverage of epithelial cells and protection from microbial infection. Co-polymers of hyaluronic acid and other polymers are also contemplated. For example, copolymers of hyaluronic acid with other saccharide polymers, and/or non-saccharide polymers such as poly(ethylene glycol) can be employed in the compositions and methods of the invention.

The invention further provides syringe-like applicators and tampons for administration of the compositions of the invention to a mammalian vagina.

Pathogens that can be treated by the compositions, methods and articles of the invention include bacteria, yeast, fungi, trichomonia and other parasites. An effective amount of the compounds of the invention can vary, but in some embodiments the effective amount can range from about 0.01 milligrams to about 500 milligrams.

DETAILED DESCRIPTION OF THE INVENTION

Figure 1:
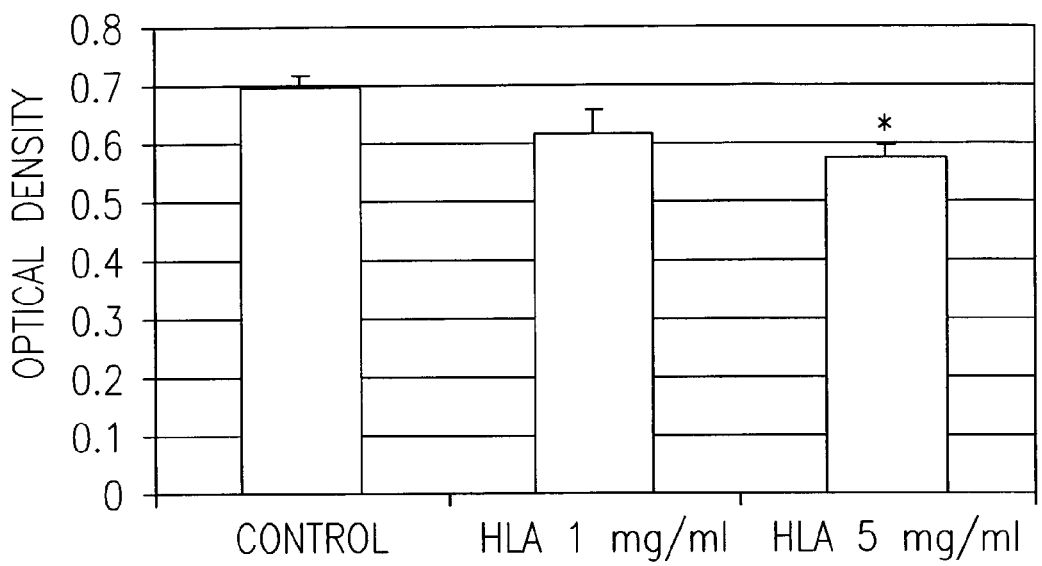
FIG. 1 is a bar graph illustrating that hyaluronic acid (HLA) prevents adherence of *E. coli* to A431 cells. The optical density at 540 nm of a 2 hr. culture of bacteria bound to A431 cells that were treated with control (PBS), 1 mg/ml HLA or 5 mg/ml HLA was used as a measure of the number of bound bacteria. The data represent mean±SEM. N=5 in each group. The symbol * represents significant difference compared to control group (p<0.05).

Urogenital infections often result from an imbalance in the types of microflora that occupy the urogenital tract, for example, a vagina with an overabundance of one type of bacteria is subject to infection by that type of bacteria as well as being more susceptible to infection by other types of bacteria, fungi and other parasites. The initial and critical step in the pathogenesis of urogenital infections involves adherence by the pathogen to the epithelium of the urogenital tract (e.g., the vagina). The invention provides compositions and methods to inhibit adherence of pathogens to the epithelium of the urogenital tract through the use of inexpensive, readily available active compounds. The compositions and methods avoid strong chemicals and unnatural substances whose effects on the health and reproduction of the user are unknown. Use of these compositions and methods improves the microenvironment in the urogenital tract, reduces the number of pathogens occupying the urogenital tract and prevents growth and attachment of an overabundance of pathogens to urogenital tissues.

Hyaluronic Acid Compounds

Hyaluronic acid (HLA), also known as hyaluronan, is a natural polysaccharide found abundantly in synovial fluid and the extracellular matrix (Luo et al., in Atala & Lanza eds., Methods in Tissue Engineering, pp. 539–553, Academic Press, 2002). Hyaluronic acid is needed for the structure and organization of extracellular matrix. Because of its excellent biocompatibility and other properties, hyaluronic acid has been used in various medical applications such as in tissue engineering, drug delivery, surgery, and cosmetics.

Natural hyaluronic acid usually consists of 200–10,000 repeating disaccharide units of (β-1,4-)-linked D-glucuronic acid and (β-1,3-)-N-acetyl-D-glucosamine. In some embodiments, the structure of the hyaluronic acid compound is generally that of formula I:

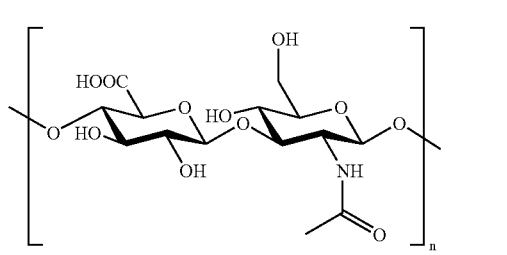

or a salt thereof, wherein n is an integer of about 2 to about 100,000. Salts of such hyaluronic acid compounds include any physiologically acceptable salt available to one of skill in art. Examples include sodium, calcium or potassium salts of hyaluronic acid.

While the molecular weight of hyaluronic acid isolated from natural sources typically ranges from about $1\times10^5$ to $5\times10^6$ daltons, the hyaluronic acid employed in the compositions of the invention can have a wide variety of molecular weights. For example, the molecular weight can vary from about $1\times10^3$ daltons to about $1\times10^8$ daltons. Hence, the value of n can vary. For example, hyaluronic acid compounds can be utilized that have as few as about two to about six units (n=about 2 to about 6), as few as about two to about ten units (n=about 2 to about 10), as few as about three to about twenty units (n=about 3 to about 20), as few as about three to about thirty units (n=about 3 to about 30), or as few as about four to about one hundred units (n=about 4 to about 100). The upper limit on the number of disaccharide units (n) for the hyaluronic acid compounds used in the invention can also vary. For example, hyaluronic acid compounds can be utilized that have as many as about one hundred to about two hundred units (n=about 100 to about 200), as many as about one hundred to about five hundred units (n=about 100 to about 500), as many as about three hundred to about one thousand units (n=about 300 to about 1000), as many as about three hundred about ten thousand units (n=about 300 to about 10,000), or as many as about four hundred to about one hundred thousand units (n=about 400 to about 100,000). Mixtures of hyaluronic acid compounds with different lengths can also be used in the compositions and methods of the invention. Therefore, the length of the hyaluronic acid compounds employed in the invention can be adjusted to obtain optimal coverage of the urogenital tract or to facilitate preparation of a composition that can readily be administered to a mammal.

Moreover, in many embodiments some of the individual sugar units of the hyaluronic acid can have a variety of substituents in place of the hydroxy (—OH), carboxylate (—COO⁻), methylenehydroxy (—CH₂—OH) and N-acetyl (—NH—CO—CH₃) substituents that are often found in hyaluronic acid preparations. For example, lower alkyl moieties can replace any of the hydrogen atoms from the hydroxy (—OH), carboxylic acid (—COOH) and methylenehydroxy (—CH₂—OH) substituents of the hyaluronic acid compounds employed in the invention. Amino or lower alkyl amino groups can replace any of the OH groups on the hydroxy (—OH), carboxylic acid (—COOH) and methylenehydroxy (—CH₂—OH) substituents of the hyaluronic acid compounds employed in the invention. Sulfate (—SO$_4^-$) can replace any of the OH groups on the hydroxy (—OH), carboxylic acid (—COOH) and methylenehydroxy (—CH$_2$—OH) substituents of the hyaluronic acid compounds employed in the invention. Hence, substituents that can be present instead of, or in addition to, the substituents shown in formula I include sulfate (—SO$_4^-$), lower alkoxy, lower alkanoyloxy, and/or lower alkanoylaminoalkyl. Other examples of modified saccharide units and methods for generating such modified saccharide units are provided in Luo et al., Modification of Natural Polymers: Hyaluronic Acid, in Atala and Lanza, eds., Methods in Tissue Engineering, 539–53, Academic Press, San Diego (2002).

As used herein, lower alkyl means (C$_1$–C$_6$) alkyl. Such (C$_1$–C$_6$) alkyl can be methyl, ethyl, propyl, isopropyl, butyl, iso-butyl, sec-butyl, pentyl, 3-pentyl, or hexyl. Preferred lower alkyl groups are (C$_1$–C$_3$) alkyl including methyl ethyl, propyl, isopropyl and the like. Lower alkoxy generally means (C$_1$–C$_6$) alkoxy; such (C$_1$–C$_6$) alkoxy can, for example, be methoxy, ethoxy, propoxy, isopropoxy, butoxy, iso-butoxy, sec-butoxy, pentoxy, 3-pentoxy, or hexyloxy. Lower hydroxy alkyl refers to a hydroxy group attached to a lower alkyl or lower alkylene group (e.g. —CH$_2$—CH$_2$—OH). Lower alkanoyloxy refers to (C$_2$–C$_6$)alkanoyloxy, for example, acetoxy, propanoyloxy, butanoyloxy, isobutanoyloxy, pentanoyloxy, or hexanoyloxy. Lower (C$_1$–C$_6$) alkanoylamino can, for example, be acetamino, propanoylamino, butanoylamino, isobutanoylamino, pentanoylamino, or hexanoylamino.

In some embodiments, one or more of the sugar units of the hyaluronic acid compounds can be replaced with a different type of saccharide unit. For example, the hyaluronic acid compounds utilized in the compositions or methods of the invention can have one or more glucose, glucuronic acid, mannose, mannuronic acid, galactose, galacturonic acid, gulose, guluronic acid, fucose, xylose, N-acetylneuraminic acid, N-acetyl glucosamine or other sugar units. The number of alternate saccharide units can vary in the variant hyaluronic acid compounds used in the invention. For example, the variant hyaluronic acid compounds can have about 0% to about 50% alternate saccharide units. In other embodiments, the variant hyaluronic acid compounds can have about 0% to about 40%, or about 30%, or about 20% or about 10% alternate saccharide units. Mixtures of hyaluronic acid compounds with different substituents and sugar units can also be used in the compositions and methods of the invention. Therefore, while the hyaluronic acid compounds employed in the invention can have disaccharide units like those depicted in formula I, some variability in the types of substituents and sugar units present in the hyaluronic acid preparation employed is acceptable so long as the preparation can inhibit binding of a pathogen. Hence, the hyaluronic acid compounds of the invention can have a variety of substituents and sugar units as well as having a variety of lengths.

In other embodiments, co-polymers of hyaluronic acid with other polymers can be employed in the compositions and methods of the invention. In some embodiments, the polymers are non-polysaccharide polymers. Examples of polymers that can be used with hyaluronic acid include poly(ethylene glycol)/poly(ethylene oxide), poly(vinyl alcohol), poly(vinylpyrrolidone), and poly(2-hydroxylethyl methacrylate). Such polymers can be covalently bonded to hyaluronic acid or simply combined with hyaluronic acid to form a mixed composition.

According to the invention, hyaluronic acid compounds, co-polymers and their salts, associate with cells in the mammalian urogenital tract and inhibit or prevent pathogens from contacting human cells/tissues. The term "mammal," as used herein, refers to an animal, in general, a warm-blooded animal. Mammals include cattle, buffalo, sheep, goats, pigs, horses, dogs, cats, rats, rabbits, mice, and humans. Also included are other livestock, domesticated animals and captive animals.

An effective amount of a hyaluronic acid compound, co-polymer, or salt thereof, for preventing urogenital infections is an amount that inhibits association (e.g. binding) of a pathogen with a mammalian epithelial cell. To achieve the desired inhibition, the composition may be administered as single or divided dosages, for example, of at least about 0.001 µg to about 100 to 200 mg, of about 0.01 µg to about 75 to 100 mg, of about 0.1 µg to about 50 to 75 mg or about 1.0 µg to about 30 to about 50 mg of one or more hyaluronic acid compound, although other dosages may provide beneficial results. In some embodiments, the dosage can vary from about 1 mg to about 50 mg.

Daily doses of the compositions of the invention can vary as well. Such daily doses can range, for example, from about 0.001 mg/day to about 500 mg/day, from about 0.01 mg/day to about 250 mg/day, from about 0.1 mg/day to about 120 mg/day, from about 0.1 mg/day to about 100 mg/day, from about 0.1 mg/day to about 75 mg/day, and from about 0.1 mg/day to about 50 mg/day of one or more of the hyaluronic acid compounds.

The amount administered will vary depending on various factors including, but not limited to, the disease, the weight, the physical condition, the health, the age of the mammal, and whether prevention or treatment of infection is to be achieved. Such factors can be readily determined by the clinician employing animal models or other test systems that are available in the art.

Several receptors exist on human cell surfaces for hyaluronic acids, such as the CD44 and RHAMM receptors. See PCT Application WO 02/24223; Goodison et al., *J. Clin. Pathol: Mol. Pathol.*, 1999, 52, 189–196; Lesley et al., *Journal of Biological Chemistry*, 2000, 275, 26967–26975; Lee & Spicer, *Current Opinion in Cell Biology*, 2000, 12, 581–586; Sackman & Bruisma, *ChemPhysChem*, 2002, 3, 262–269. The CD44 receptor is a ubiquitously expressed family of cell surface adhesion proteins. Cells not expressing CD44 usually have other similar receptors. For example, lymphatic vessel endothelial cells have LYVE proteins that may bind hyaluronic acids.

While the hyaluronic acid compounds of the invention may bind to such receptors, the efficacy of the compositions and methods of the invention does not necessarily depend upon such binding. For example, the hyaluronic acid compounds of the invention prevent adherence of *Escherichia coli* and *Candida albicans* cells to mammalian epithelial cells, but neither *Escherichia coli* nor *Candida albicans* cells is believed to bind mammalian epithelial cells through the CD44 receptor. Hence, the mechanism by which hyaluronic acid compounds prevent adherence of pathogens is not believed to depend on blocking the human cell receptors specifically used for pathogen attachment. Instead, hyaluronic acid and its derivatives may generally attach to a cell surface, form a physical shield, and prevent pathogens from binding to cell surfaces.

Pathogens

One mechanism by which pathogens adhere to host tissue cells is through protein-sugar interactions. For examples, adherence of *Candida albicans* onto female genital tract cells involves binding between proteins on the fungal cell surface and fucose-containing glycosides on epithelial surface. The adherence of uropathogenic *E. coli* to the urinary tract involves binding of bacterial PapG Adhesin and FimH adhesin proteins to epithelial cell surface sugar residues (for example, Gal($\alpha$1,4)Gal from glycolipids and mannose-residues on the mammalian cell surface). The adherence of *Chlamydia trachomatis* to the genital tract involves binding between a *Chlamydia* surface polysaccharide (containing 7–9 mannose residues) and mannose-binding proteins on the host cell surface. Adherence of *Mycoplasma bovis* to the genital and urinary tract involves binding between bacterial surface proteins and sialic acid residues on the host cell surface. Urinary tract infection by *Staphylococcus saprophyticus* involves the binding between bacterial surface lectins and the GalNac residues on the host cell surface. Another mechanism of bacterial adherence to host tissues is through non-specific binding, for example, by hydrogen-bonding and divalent-cation-mediating binding between the glycocalyx layers of bacteria and host cells. A good pathogen adhesion inhibiting system prevents both the specific and the non-specific binding of pathogens to vaginal and urinary tract cell surfaces.

According to the invention, adherence by any pathogen can be inhibited by the compositions and methods of the invention. Such pathogens can be fungi, bacteria, trichomonia or other parasites. Adherence of urogenital *Candida*, bacteria, chlamydia, trichomonia, and gonorrhea can be inhibited.

Genital candidiasis, generally known as yeast infection, is the infection of the genital tract caused by *Candida albicans*. Women suffering from yeast infection usually develop vulval irritation, itching and vaginal discharge, the vaginal wall is covered with a white cheesy material, and the vulva is reddish and swollen. Infections by *Candida albicans* can be inhibited by the compositions and methods of the invention.

Bacterial infections by bacteria such as *Escherichia coli, Gardnerella vaginalis, Mycoplasma bovis, Mycoplasma hominus, Neisseria gonorrhoeae, Staphylococcus saprophyticus,* can also be inhibited by the compositions and methods of the invention.

Chlamydial infections are sexually transmitted nongonococcal infections caused by *Chlamydia trachomatis*. These infections include nongonococcal urethritis, mucopurulent cervicitis and nonspecific genital infections. Typically, the affected individual suffers from vaginal discharge, dysuria and cervicitis with yellow, mucopurulent secretion. Infections by *Chlamydia trachomatis* can also be inhibited by the compositions and methods of the invention.

Trichomoniasis is caused by a flagellate anaerobic protozoan *Trichomonas vaginalis*. The trichomoniasis is accompanied by a copious, greenish-yellow, frothy vaginal discharge associated with irritation, itching and soreness of the vulva and thighs. The vaginal walls and cervix surface show punctuate red spots. Infections by *Trichomonas vaginalis* can also be inhibited by the compositions and methods of the invention.

Administration

The compositions of the invention can be administered for prophylactic, therapeutic, and/or hygienic use. Such administration is generally topical, particularly to epithelial surfaces of the urogenital tract, especially the mucosal surfaces of the urogenital tract. Epithelial surfaces of the urogenital tract that can be treated with the compositions and methods of the invention include rectal, urethral, ureteral, vaginal, cervical, uterine, etc. In some embodiments, the epithelial surface is vaginal.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. For prevention of urogenital diseases, administration of the compositions of the invention may be essentially continuous over an indeterminate period of time, for example, at regular intervals for life. Alternatively, the compositions of the invention can be administered continuously for a pre-selected period of time or in a series of spaced doses. Local administration is generally contemplated.

The compositions are prepared by combining the active ingredients in the appropriate concentrations. Other active or inactive agents selected by one of skill in the art can optionally be added. The absolute weight of a given active agent included in a unit dose can vary widely.

The compositions of the invention can be administered to the urogenital tract in the form of an article or carrier such as an insert, syringe-like applicator, tablet, suppository, pessary, powder/talc or other solid, solution, liquid, spray, aerosol, douche, ointment, tampon, foam, cream, gel, paste, microcapsules, vaginal sponge, vaginal ring, controlled release formulation, sustained release formulation or bioadhesive gel (e.g., a mucoadhesive thermogelling composition (see, for example, U.S. application Ser. No. 10/135,805, filed on Apr. 30, 2002, which is incorporated herein by reference)).

For intravaginal administration, the therapeutic agents may be formulated as is known in the art for direct application to the vaginal area. Forms chiefly conditioned for vaginal application take the form, for example, of creams, milks, gels, dispersion or micro-emulsions, lotions thickened to a greater or lesser extent, impregnated pads, ointments, aerosol formulations (e.g., sprays or foams), creams, lotions, pastes, jellies, sprays, and aerosols. Alternatively, the composition can be formulated to be part of an adhesive polymer, such as polyacrylate or acrylate/vinyl acetate copolymer.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays are conveniently delivered from pressurized packs, for example, via a specially shaped closure. The active compositions can also be delivered via iontophoresis, e.g., as disclosed in U.S. Pat. Nos. 4,140,122; 4,383,529; or 4,051,842. The percent by weight of a prophylactic agent of the invention present in a vaginal formulation will depend on various factors, but generally will be from about 0.01% to about 98% of the total weight of the formulation, and typically about 0.1 to about 90% by weight.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions with a pH of about 4.5 to about 5.5.

Furthermore, the active ingredients may also be used in combination with other therapeutic agents, for example, anti-microbial agents, pain relievers, anti-inflammatory agents, vitamins (e.g., vitamin B, C or E), aloe vera and the like, whether for the conditions described or some other condition.

The present invention further pertains to a packaged pharmaceutical composition for controlling or preventing microbial infection such as a kit or other container. The kit or container holds a therapeutically effective amount of a pharmaceutical composition for preventing, controlling or inhibiting microbial infection and instructions for using the pharmaceutical composition for prevention, control or inhibition of microbial infection. The pharmaceutical composition includes a composition of the present invention, in a therapeutically effective amount such that vaginal infection is prevented, controlled or inhibited.

In addition, the invention provides a vaginal insert that can release the hyaluronic acid compounds in a controlled fashion. Such a vaginal insert can be biodegradable or non-biodegradable. The vaginal insert provides sustained release of the active ingredients at an appropriate rate for achieving the desired degree of inhibition of pathogen attachment.

In some embodiments, the active ingredients can be formulated with oleaginous bases or ointments to form the vaginal insert. This class of formulations comprises the active ingredients and hydrocarbon-based semisolids containing dissolved and/or suspended bacteriostats/preservatives and a buffer system. The petrolatum component in these bases can be any paraffin ranging in viscosity from mineral oil employing incorporated isobutylene, colloidal silica, or stearate salts to paraffin waxes. White and yellow petrolatum are examples of such systems. Bases of this class can be made by incorporating high-melting waxes into a fluid mineral oil via fusion or by incorporation of polyethylene into mineral oil at elevated temperature. Polysiloxanes (also known as silicones) are suitable for use in these bases and typically have a viscosity in the range of about 0.5 to $10^6$ centistokes. The organic entities attached to the polysiloxane are preferably lower molecular weight hydrocarbon moieties having from 1 to 8 carbons each, such as lower alkyl, lower alkenyl, phenyl and alkyl substituted phenyl, and phenyl (lower)alkyl, such as benzyl. In such a moiety, each lower alkyl or alkenyl group preferably has 1 to 3 carbons inclusive, such as in a dimethylsiloxane polymer.

Absorption bases can be used with such an oleaginous system. In addition to the active ingredients, additional ingredients with the capacity to emulsify a significant quantity of water are employed. Water-in-oil (w/o) emulsions can be formed wherein the external phase is oleaginous in character. Preservatives/bacteriostats, such as the parabens, buffer systems, etc. can be incorporated into these bases as emulsified aqueous solutions together with the active ingredient. Diverse additives are conveniently used as the emulsifier, and these include, but are not limited to, cholesterol, lanolin (which contains cholesterol and cholesterol esters and other emulsifiers), lanolin derivatives, beeswax, fatty alcohols, wool wax alcohols, low HLB (hydrophobe/lipophobe balance) emulsifiers, and assorted ionic and nonionic surfactants, singularly or in combination.

Water-In-Oil (W/O) emulsion bases can be employed in the urogenital compositions and inserts of the invention. These formulations can be an expansion of the general class of absorption bases that includes liquids or creams. They can be prepared by taking a mixture of the active ingredients with oil phase ingredients, bacteriostats/preservatives and buffer salts that are dissolved or suspended therein and to which water has been added to form a water-in-oil emulsion.

Oil-In-Water (O/W) emulsion bases can also be utilized in the vaginal compositions and inserts of the invention. These systems are semisolid emulsions, micro-emulsions, or foam emulsion systems. Usually such a system has a "creamy white" appearance. Typically, the internal oil phase is in the range in percentage composition of about 10% to about 40% oil by weight and the external phase may contain 80% or more water. The oleaginous phase may contain, but is not limited to, long-chain alcohols (cetyl, stearyl), long-chain esters (myristates, palmitates, stearates), long-chain acids (palmitic, stearic), vegetable and animal oils and assorted waxes. These can be made with anionic, cationic, nonionic or amphoteric surfactants, or with combinations especially of the nonionic surfactants. The examples below are exemplary of these systems, but those skilled in the art will appreciate that substitutions and additions or omissions of the specified components could be made by one who is skilled in the art.

Urogenital inserts and suppositories containing the active ingredients can be, for example, oleaginous in nature that melt at body temperature, or polyethylene glycol-based compositions that dissolve in urogenital (e.g. vaginal) fluids. Additional bases for suppositories are glycerin and glycerinated gelatin.

The active ingredients can also be formulated into urogenital (e.g. vaginal) inserts using buffered gels made with gelling agents. Some examples of these gelling agents are: cellulosics, cationic polymers, polyoxyalkylenes, and carboxyvinyl polymers. Cellulosics useful in the formulations of the invention include, for example, methyl cellulose, carboxymethyl cellulose, hydroxyethyl cellulose, and hydroxypropyl cellulose. Cationic Polymers useful in the formulations of the invention include "Polyquaternium-10", a polymeric quaternary ammonium salt of hydroxyethyl cellulose reacted with a trimethyl ammonium-substituted epoxide, and the like. Polyoxyalkylenes useful in the invention include polyoxyethylene-polyoxypropylene esters of lanolin and derivatives thereof. Carboxyvinyl polymers useful for the formulations of the invention include cross-linked acrylic acid polymers, e.g., those commercially available from B.F. Goodrich Co., Akron, Ohio, under the designation CARBOPOL™.

Controlled or sustained release can be achieved by the addition of time-release additives, such as polymeric structures, matrices, that are available in the art. For example, the compositions of the invention may also be administered through the use of hot-melt extrusion articles, such as bioadhesive hot-melt extruded film (see, for example, U.S. Pat. No. 6,375,963, which is incorporated herein by reference). The formulation can comprise a cross-linked polycarboxylic acid polymer formulation, generally described in U.S. Pat. No. 4,615,697 to Robinson (hereinafter "the '697 patent"), which is incorporated herein by reference. In general, about eighty percent of the monomers of the polymer in such a formulation contain at least one carboxyl functionality. The cross-linking agent should be present at such an amount as to provide enough adhesion to allow the system to remain attached to the target epithelial surfaces for a sufficient time to allow the desired release of hyaluronic acid to take place.

A urogenital insert can comprise a mixture or coating of polymers that provide release of the active agents at a constant rate over a prolonged period of time. In some embodiments, the urogenital (e.g. vaginal) insert comprises water-soluble pore forming agents, such as polyethylene glycol (PEG) that can be mixed with water insoluble polymers to increase the durability of the insert and to prolong the release of the active ingredients. Such a water-soluble pore-forming agent can be polyethylene glycol, polypropylene glycol, a mixture or polymer of sugars (lactose, sucrose, dextrose, etc.), salts, poloxamers, hydroxypropylcellulose, polyvinyl alcohol and other water-soluble food grade and other excipients.

When PEG is used as a pore forming agent, the molecular weight of PEG is in the range from about 200 to about 20,000, alternatively, from about 400 to about 8,000. For example, PEG having a molecular weight of about 540 to about 8,000 is used. In another embodiment, the PEG has a molecular weight of about or above 1,000 to about 8,000. The molecular weight of PEG used for the coating with the formulation of the invention will depend on the ability of PEG to form a coating film that is non-sticky, having enough strength and creating adequate pore size for controlling the release of active ingredients over the desired time period both in vitro and in vivo.

The pore-forming agent is used in the formulation of the invention in the amount effective to regulate the release of a hyaluronic acid compound at a desired rate. Preferably, the effective amount of the pore-forming agent provides long term delivery of the active agent thus increasing the useful life of a sustained-release insert or implant. The effective amount of the pore forming agent will depend on the desired rate and duration of the release and the ability to form a continuous microporous film during the coating process. To enable release duration over longer periods of time PEG with higher molecular weights is used. For example, PEG 8000 can provide release over a period of time that is longer than 100 days, when used in a concentration from 10 to 50%, preferably from 20 to 45% and most preferably from 30 to 45%. The concentration of PEG is expressed herein in % weight per dry basis and represents the concentration of PEG in the coating film after drying. Similarly, the thickness of the coating film is from 5 to 50 µm, preferably 30 from 10 to 30 µm and most preferably from 15 to 25 µm.

A good correlation exists between the dissolution rate of active agents and the amount of pore forming agent incorporated in the coating film based on in vitro and in vivo studies. Depending on the desired length of release, the PEG concentration ranges can be adjusted as needed. For example, in vivo duration of a coated insert may be predicted simply from the in vitro dissolution rate of the active agent at the 120-hour time point.

The urogenital (e.g. vaginal) insert of the invention may also comprise a water insoluble polymer. Examples of such polymers are ethylcellulose, acrylic resins, co-polymer of methacrylic acid and acrylic acid ethyl ester, polylactic acid, PLGA, polyurethane, polyethylene vinyl acetate copolymer, polystyrene-butadiene copolymer and silicone rubber, or mixtures thereof. For example, polymers sold under trade names Aquacoat ECD 30 and Eudragit RS 30 and NE 30D (registered trademarks of Rhom Tech, Inc.) can be used.

A polymer suitable for use in this invention is a polymer that is capable of forming a continuous coating film during the process of spraying and drying with a pore-forming agent. The rate controlling film prepared with such a polymer is very stable during implantation. The film should have enough strength to withstand tear and inner osmotic pressure, and have the stability not to swell or hydrate during the implantation life.

In one embodiment, the coating formulation of the invention is used to coat pellets comprising the active ingredients that are compressed to form a solid, biodegradable insert and then administered for inhibiting infection.

A polymer formulation can also be utilized to provide controlled or sustained release. Such a polymer formulation can be adjusted to control the release rate of the hyaluronic acid by varying the amount of cross-linking agent in the polymer. Suitable cross-linking agents include divinyl glycol, divinylbenzene, N,N-diallylacrylamide, 3,4-dihydroxy-1,5-hexadiene, 2,5-dimethyl-1,5-hexadiene and similar agents.

One example of a polymer for use in such a formulation is Polycarbophil, U.S.P., which is commercially available from B.F. Goodrich Specialty Polymers of Cleveland, Ohio under the trade name NOVEON™-AA1. The United States Pharmacopeia, 1995 edition, United States Pharmacopeial Convention, Inc., Rockville, Md., at pages 1240–41, indicates that polycarbophil is a polyacrylic acid, cross-linked with divinyl glycol.

Other useful bioadhesive polymers that may be used in such a drug delivery system formulation are mentioned in U.S. Pat. No. 4,615,697. For example, these include polyacrylic acid polymers cross-linked with, for example, 3,4-dihydroxy-1,5-hexadiene, and polymethacrylic acid polymers cross-linked with, for example, divinyl benzene. Typically, these polymers would not be used in their salt form, because this would decrease their bioadhesive capability. Such bioadhesive polymers may be prepared by conventional free radical polymerization techniques utilizing initiators such as benzoyl peroxide, azobisisobutyronitrile, and the like. Exemplary preparations of useful bioadhesives are provided in the '697 patent.

For vaginal administration, the formulation preferably remains attached to the epithelial surfaces for a period of at least about eight to about forty-eight hours. Such results may be measured clinically over various periods of time, by testing samples from the vagina for hyaluronic acid. Such bioadhesion can be attained with bioadhesive polymers using a cross-linking agent that is present at about 0.1 to 6.0 weight percent of the polymer, with about 1.0 to 2.0 weight percent in some embodiments, to achieve an appropriate level of bioadhesion. Bioadhesion can also be measured by commercially available surface tensiometers utilized to measure adhesive strength.

The formulation may be in the form of a gel, cream, tablet, pill, capsule, suppository, film, or any other pharmaceutically acceptable form that is tolerated by the mucosa and does not wash away easily. Different formulations are further described in U.S. Pat. No. 4,615,697, which is incorporated herein by reference.

As will be apparent to those skilled in the art, the composition of the formulation can be varied to affect certain properties of the formulation. For example, the viscosity can be varied by varying the concentration of hyaluronic acid or by adding a polymer or gel former. In some embodiments, a bioadhesive polymer can be included at various concentrations to provide greater or lesser bioadhesion. A pH sensitive bioadhesive can be utilized to effect greater release at certain pH values (e.g. higher pH values indicative of infection). One useful aspect of bioadhesive compositions is that they can be effectively administered even during menses. The particular bioadhesive qualities prevent the composition from being diluted or washed away, thereby increasing the utility of the present formulation.

Liquid compositions of the invention can be administered from absorbent materials, such as a tampon or sponge, or as a spray/aerosol (applied to the affected area using a pump-type or aerosol sprayer). The use of a tampon, in which the intravaginal composition of the invention has been incorporated, is advantageous in that it the composition will be slowly and continuously released even though it may be continuously carried away by menstrual blood or other vaginal discharge. Providing the composition in the form of a solution, which may initially be provided in a concentrated liquid form, or as a dissolvable powder, tablet or the like requiring the addition of water, saline or other suitable diluents prior to use, enables the composition to be administered as a vaginal douche.

Solid compositions of the invention can be applied by any number of means, including the use of applicators or by patient self-insertion. For example, creams, lotions, suppositories, foams, pastes, ointments, gels, tablets, or tampons may be applied to the vagina using an applicator, such as a squeeze-type or plunger-type applicator available for use in applying vaginal products. Administering the composition as a suppository is advantageous as it provides convenience, ease of application, increased safety and/or neatness. Administering the composition as a cream having low surface tension is advantageous as it provides a uniform wetting action that assists in composition penetration into vaginal crypts and crevices and can act as a moisturizer.

Additionally, additives may be mixed in with the formulation for maximum or desired efficacy of the delivery system or for the comfort of the patient. Such additives include, for example, lubricants, plasticizing agents, preservatives, gel formers, tablet formers, pill formers, suppository formers, film formers, cream formers, disintegrating agents, coatings, binders, vehicles, coloring agents, taste and/or odor controlling agents, humectants, viscosity controlling agents, pH-adjusting agents, and similar agents.

Figure 5:
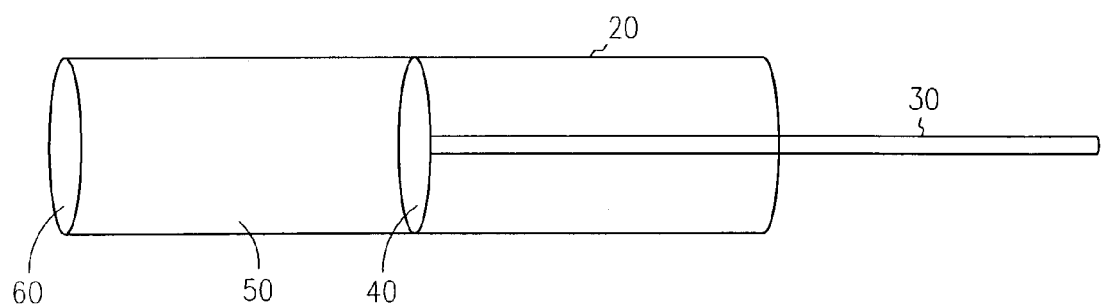
FIG. 5 is a schematic diagram of one type of syringe-like applicator that can be used to deliver a hyaluronic acid composition to a vagina of a mammal. The syringe-like applicator consists of a barrel 20 and a plunger 30 with a plunger head 40. The syringe-like applicator can also have a barrier seal 60 distal to the plunger head 40 and a chamber 50 within the barrel that lies between the plunger 30 and the barrier seal 60. The chamber 50 comprises an effective amount of a hyaluronic acid compound or a salt thereof. The presence of the barrier seal 60 seals the applicator and keeps the composition contained with the applicator during shipping and handling. The barrier seal 60 can be removed by the user, or it can rupture when the user depresses the plunger. At the time of use, the applicator is inserted into the vagina and the plunger 30 is depressed. This force will push the composition out of the applicator and into the vagina.

One desirable embodiment provides for compositions of the invention in a syringe-like applicator (also known as a plunger-type or syringe-like applicator (see FIG. 5)). For example, a composition including hyaluronic acid may be placed into a chamber 50 within the barrel 20 of a syringe-like applicator. The chamber is sealed at the distal end with a barrier seal 60 and at the proximal end by the plunger head 40. The presence of the barrier seal 60 seals the applicator and keeps the composition contained with the applicator during shipping and handling. However, the barrier seal 60 can be removed by the user or it can rupture when the user depresses the plunger 30. At the time of use, the applicator is inserted into the vagina and the plunger 30 is depressed. This force will push the composition out of the applicator and into the vagina.

Figure 6:
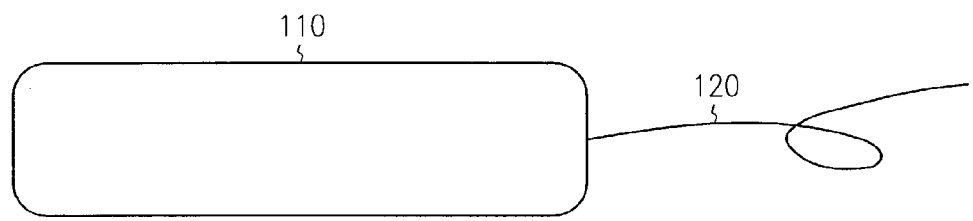
FIG. 6 is a schematic diagram of a tampon that can be used to deliver a hyaluronic acid composition to the vagina of a mammal. The tampon consists of a tubular shaped material 110 comprising a hyaluronic acid compound and a string 120 or other attachment for retrieval or positioning of the tampon within the vagina.

Another desirable embodiment provides for compositions of the invention in combination with a tampon (FIG. 6). For example, hyaluronic acid is applied to tampon material 110 as a solution and dried on the fibers. Alternatively, the hyaluronic acid may be mixed with sustained release materials (e.g. polymers) and/or a carrier, then shaped into a tampon-like article (e.g. as shown in FIG. 6) for application to the vaginal tract. A string (120; FIG. 6), or other convenient attachment and retrieval device, can be used for easy removal of the tampon. The applicator and tampon are prepared in a sterile manner, or sterilized after packaging.

One embodiment of the invention provides an aqueous gel containing a mucoadhesive material, such as carboxymethylcellulose (optionally mixed with a thermogelling mucoadhesive agent), to be mixed with hyaluronic acid to thereby form a composition of the invention. An additional embodiment provides for the encapsulation of hyaluronic acid in polymeric microparticles. Once in situ, the polymer dissolves and the hyaluronic acid is released. In this case, release of hyaluronic acid can be controlled by the microparticles to provide extended production of the desired product (e.g., sustained release). The delivery vehicle is not limited to use in the vagina, but could also be applied to a wide variety of biomedical applications where delivery of hyaluronic acid is desired. Appropriate modification of the delivery vehicles described herein is within the skill of those in the art.

Additionally, the composition and/or delivery materials may contain additional beneficial agents that can improve the vaginal environment. For example, polymers used as carrier or for encapsulation or for sustained release may be hydrolytically degraded into an acid or acid producing species. One such polymer is a poly (vinyl alcohol) backbone with pendant polycaprolactone chains that, upon disintegration, yields poly [vinyl (polycaprolactate)]. The polycaprolactone is hydrolytically degraded into caproic acid. This acid aids in lowering pH and controlling harmful bacterial growth, thus helping to restore balance to the vaginal system. In addition, this material is melt processable and can be formed into a system for controlled delivery of the hyaluronic acid. Additionally, a peroxide of Laureth-4 (e.g., a Laureth-4 terminal peroxide) would release laureth-4 and peroxide (e.g., hydrogen peroxide). Laureth-4 decreases TSS-1 production by *S. aureus* and the peroxide is available to suppress undesirable anaerobes and *Gardnerella vaginalis*, thus reducing toxin production while reestablishing the vaginal flora.

The Examples further illustrate certain aspects of the invention and are not intended to limit the invention in any manner.

EXAMPLE 1

Effect of Hyaluronic Acid on *E. coli* Adhesion to Epithelial Cells

This Example illustrates that *E. coli* have reduced adhesion to substrates containing hyaluronic acid. *E. coli* causes 80% of all urinary tract infections. Vaginal colonization by *E. coli* is generally correlated with development of ascending urinary tract infections, which affect 10%–20% of women at some time in their life and cost $3 billion per year in healthcare expenditures. Moreover, colonization of *E. coli* in the vagina is also the major cause, along with the Group B streptococci, of neonatal meningitis. As the recurrences of both vaginal and urinary tract infections are frequent following the initial episode, prevention of such infections is important.

Materials and Methods

Cultured A431 cells were used as a vaginal epithelial model. A431 cells were obtained from American Cell Type Culture Collection, catalog # CRL-1555. A monolayer of A431 cells was grown on a 24-well tissue culture plate until confluent.

*E. coli* with P family pili, ATCC 53505, were cultured in trypticase soy broth (TSB) overnight. Phosphate buffered saline (PBS, control) or hyaluronic acid (Sigma catalog # H 1876) solutions at a concentration of 1 mg/ml or 5 mg/ml in PBS was added to the A431 cell layers, using a volume of 1.2 ml/well. After incubation for 30 minutes at 37° C., 0.7 ml of solution was removed from the wells and 0.5 ml of the bacteria suspension was added. The bacterial suspension employed had an optical density of 1.0 at 540 nm. After 60 minutes, the supernatant in each well was removed and the wells were rinsed thoroughly with PBS to remove all non-bound bacteria. Trypticase soy broth was then added to wells, and the whole system was incubated at 37° C. with shaking for 2 hours. Bacterial concentration was measured by the detection of optical density of bacterial suspension at 540 nm.

All the data are expressed as mean±SEM and were analyzed by one-way Analysis of Variance (ANOVA) followed by a Tukey-Kramer Multiple Comparisons Test. Differences were considered significant at the level of $p<0.05$.

Results

FIG. 1 graphical illustrates the results of the *E. coli* adhesion test. Hyaluronic acid at a concentration of 5 mg/ml significantly inhibited the number of *E. coli* attached to A431 cells. A concentration of 1 mg/ml hyaluronic acid had a lesser effect on *E. coli* adhesion. This result was repeated twice and similar effects were obtained each time.

EXAMPLE 2

Effect of Hyaluronic Acid on *E. coli* Growth

This Example illustrates that the decreased adherence of *E. coli* to A431 cells was not due to an inhibitory effect by hyaluronic acid on *E. coli* growth.

Materials and Methods

To test whether hyaluronic acid could influence cellular growth, *E. coli*, ATCC 53505 cells were cultured overnight in trypticase soy broth. The culture was then diluted to an optical density of 0.1 and hyaluronic acid (1 mg/ml or 5 mg/ml) in PBS was incubated with the *E. coli* suspension. A control comprising a suspension *E. coli* treated with PBS was also prepared. The test and control cells were incubated at 37° C. with shaking and the optical density of the bacterial suspensions at 540 nm was measured at 1, 2 and 3 hours after addition of the hyaluronic acid or PBS.

All the data are expressed as mean±SEM and were analyzed by one-way Analysis of Variance (ANOVA) followed by a Tukey-Kramer Multiple Comparisons Test. Differences were considered significant at the level of $p<0.05$.

Results

Figure 2:
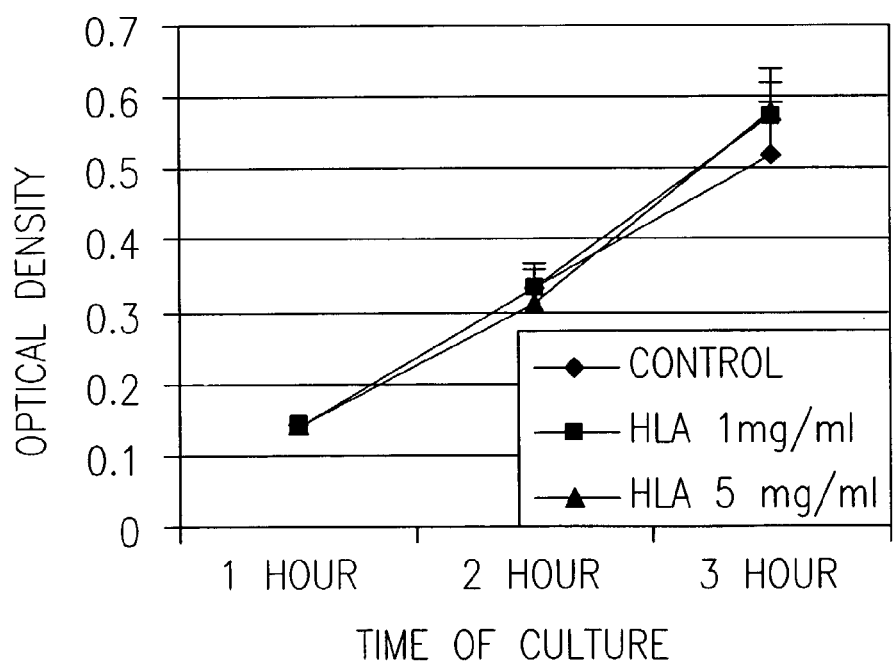
FIG. 2 illustrates that hyaluronic acid (HLA) at dosages of either 1 mg/ml or 5 mg/ml does not inhibit growth of *E. coli*. The graph plots optical density at 540 nm as a function of time for *E. coli* cultured in the presence of PBS (control), 1 mg/ml HLA or 5 mg/ml HLA.

The results on the effect of hyaluronic acid on growth of *E. coli* are shown in FIG. 2. As illustrated in FIG. 2, neither of the hyaluronic acid solutions had any effect on bacterial growth. *E. coli* exposed to PBS (control) grew well under the experimental conditions. Growth of these control cells was similar to growth of cells exposed to hyaluronic acid at either 1 mg/ml or 5 mg/ml. These data indicate that the inhibition of *E. coli* attachment to A431 cells shown in Example 1 and FIG. 1 was not due to inhibition of bacterial cell growth.

EXAMPLE 3

Effect of Hyaluronic Acid on Adherence of *Candida albicans* to A431 Cells

This Example illustrates that hyaluronic acid inhibits adherence of *Candida albicans* to mammalian epithelial cells. *Candida albicans* is the most prevalent pathogen that causes vaginitis. Hence, use of hyaluronic acid may inhibit colonization of the mammalian vagina by *Candida albicans*.

Materials and Methods

A culture of *Candida albicans*, ATCC 10231, was started as a frozen bead in peptone/glucose culture medium and incubated at 37° C. with shaking for three days before the experiment. A monolayer of A431 cells, ATCC CRL-1555, was grown on a 24-well tissue culture plate until confluent. Hyaluronic acid at concentration of 1 mg/ml PBS or 5 mg/ml PBS was added to the wells (1.2 ml/well), and the plates were incubated for 30 minutes at 35° C. A control plate of confluent A431 cells was also prepared that received 1.2 ml/well PBS and no hyaluronic acid. After the 30 min incubation, 0.7 ml of solution was removed from the wells and 0.5 ml of yeast suspension ($1\times10^6$ cfu/ml) was added. After 2 hours of incubation, the supernatant was removed from the wells and the wells were rinsed thoroughly with PBS to remove all non-bound yeast. Then, 0.2 ml of 0.25% trypsin/EDTA was added to each well and the plates were incubated at 35° C. for 15 min. Trypsinization was stopped by adding 1 ml of 10% fetal bovine serum in culture medium. The trypsinized cell/yeast suspension was centrifuged and re-suspended in 1 ml of the medium. Serial dilutions of the *Candida albicans*/A431 cell suspension were plated on Sabouraud's dextrose agar plates and incubated overnight at 35° C. The number of colonies on each plate was counted and the number of yeast attached to the cells in each well was calculated.

All the data are expressed as mean ±SEM and were analyzed by one-way Analysis of Variance (ANOVA) followed by a Tukey-Kramer Multiple Comparisons Test. Differences were considered significant at the level of $p<0.05$.

Results

Figure 3:
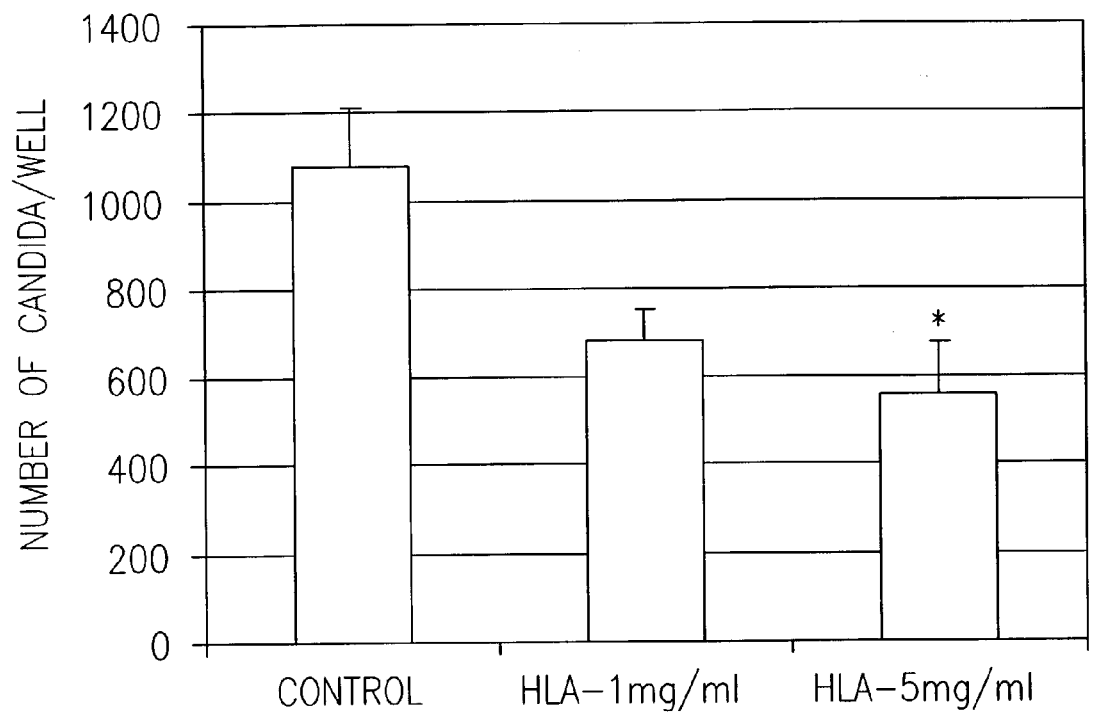
FIG. 3 is a bar graph illustrating that hyaluronic acid (HLA) prevents adherence of *Candida albicans* to A431 cells. A431 cells were treated with control (PBS), 1 mg/ml HLA or 5 mg/ml HLA prior to exposure to *Candida albicans*. The data represent the number (mean±SEM) of yeast attached to A431 cells in each well. * represents significant decrease compared to control group (p<0.05).
Figure 4:
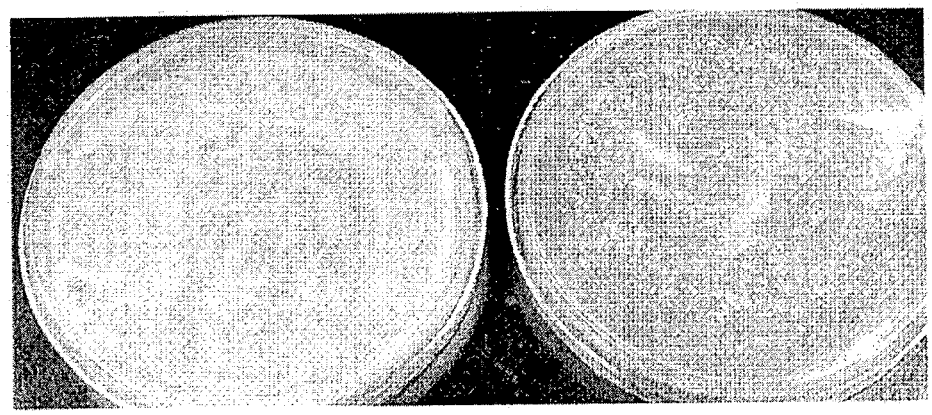
FIG. 4 shows the number of yeast colonies from PBS-treated A431 cells (left plate, control) and from hyaluronic acid-treated A431 cells (right plate). As shown, fewer yeast colonies were present when the A431 cells were treated with hyaluronic acid (right plate).

FIG. 3 summarizes the data obtained on the effects of hyaluronic acid on *Candida albicans* adherence to A431 cells. As shown in FIG. 3, the number of *Candida albicans* adhering to A431 cells was significantly inhibited by the presence of 5 mg/ml hyaluronic acid, while at a lower concentration of 1 mg/ml hyaluronic acid, the effect was not so significant. This experiment was repeated and a similar result was obtained. FIG. 4 further illustrates this effect, showing that the number of yeast colonies from PBS-treated A431 cells (control) was much higher than the number of yeast colonies obtained from hyaluronic acid-treated A431 cells.

The results provided herein therefore demonstrate that hyaluronic acid effectively inhibits the adherence of *Candida albicans* and *E. coli* to A431 cells. This cell line has been widely used as an in vitro human epithelial cell model. The inhibitory effect of hyaluronic acid on bacterial/cell attachment was not caused by inhibition of bacterial growth.

REFERENCES

1. P R Murray, K S Rosenthal, G S Kobayashi and M A Pfaller, *Medical Microbiology* (4th edition), Mosby, St. Louis, 2002.
2. A A Salyers and D D Whitt, *Bacterial Pathogenesis* (2nd edition), ASM Press, Washington D.C., 2002.
3. M W Hornef, M J Wick, M Shen and S Normark, Bacterial strategies for overcoming host innate and adaptive immune response, *Nature Immunology*, 2002, 3, 1033–1040.
4. W L Chafein, J L Lopez-Ribot, M Casanova, D Gozalbo and J P Martinez, Cell wall and secreted proteins of *Candida albicans*: identification, function and expression, *Microbiology and Molecular Biology Reviews*, 1998, 62, 130–180.
5. D Petrin, K Delgaty, R Bhatt and G Garber, Clinical and microbiological aspects of *Trichomonas vaginalis*, *Clinical Microbiology Reviews*, 1998, 11, 300–317.
6. M W Cunningham, Pathogenesis of group A Streptococcal infections, *Clinical Microbiology Reviews*, 2000, 13, 470–511.

7. I Muhldorfer, W Ziebuhr and J Kacker, *Escherichia coli* in urinary tract infections, in M Sussman edited *Molecular Medical Microbiology*, Chapter 81, Academic Press, San Diego, 2001.
8. S Mobastery and E F Azucena Jr., Bacterial antibiotic resistance, in *Encyclopedia of life Sciences*, Nature Publishing Group, 2002.
9. C Walsh, Molecular mechanisms that confer antibacterial drug resistance, *Nature*, 2000, 406, 775–781.
10. M Shnayerson, The killer bug, *Fortune* (Industrial Edition), 2002, 146(6), 149–156.
11. S J Hultgren, C H Jones and S Normark, Bacterial adhesins and their assembly, in F C Neidhardt (editor-in-chief), *Escherichia coli and Salmonella*, pp. 2730–2756, ASM Press, 1996.
12. H Connell, W Agace, M Hedlund, P Klemm, M. Shembri and C Svanborg, Fimbriae-mediated adherence induces mucosal inflammation and bacterial clearance, in Khane and Ofek edited *Toward Anti-adhesion Therapy for Microbial Diseases*, pp. 73–80, Plenum Press, 1996.
13. N Sharon, Bacterial lectins, cell-cell recognition and infection diseases, *FEBS Lett.*, 1987, 217, 145–157.
14. I Ofek and N Sharon, Adhesins as lectins: specificity and role in infection, *Current Topics in Microbiology and Immunology*, 1990, 151, 91–113.
15. M Mammen, S K Choi and G M Whitesides, Polyvalent interactions in biological systems: implications for design and use of multivalent ligands and inhibitors, *Angew. Chem. Intl. Ed.*, 1998, 37, 2754–2794.
16. D Zopf and S Roth, Oligosaccharide anti-infective agents, *Lancet*, 1996, 347, 1017–1021.
17. A Varki, Biological roles of oligosaccharides: all of the theories are correct, *Glycobiology*, 1993, 3, 97–130.
18. R G Carson, A Hung, K M Schiling and S R Wu, Oral hygiene compositions containing glyceroglycolipids as antiplaques compounds, U.S. Pat. No. 5,409,902, filed on Dec. 31, 1991.
19. A Gaffar, R Gibbsons and S Tylewska, Glycoconjugate inhibition of *Streptococcus pyrogenes* adhesion, U.S. Pat. No. 5,401,723 filed on Dec. 02, 1992.
20. DA Zopf, OM Simon, S Roth, EJ McGuire and DH Langer, Method for inhibiting *H. Pylori* infection in mammalian tissue, U.S. Pat. No. 5,883,079 filed on May 12, 1998.
21. A Gaffar, RJ Gibbsons and S Tylewksa, Oligosaccharide inhibition of *Streptococcus pyrogens* adhesion, U.S. Pat. No. 5,002,759 filed on Jul. 25, 1989.
22. P A Mardh and S Svensson, Therapeutic treatment employing oligosaccharides, U.S. Pat. No. 4,665,060 filed on Mar. 22, 1983.
23. GP Kallenius, KA Lunblad, NR Mollby, SB Svesson and J Winberg, U.S. Pat. No. 4,762,824 filed on Aug. 01, 1986.
24. Y Luo, KR Kirker and GD Prestwich, Modification of natural polymers: hyaluronic acid, in Atala and Lanza eds., *Methods in Tissue Engineering*, pp. 539–553, Academic Press, 2002.
25. MR Wessels and C Cywes, Prevention and treatment of streptococcal and staphylococcal infection, PCT Application WO 02/24223 filed on Sep. 21, 2001.
26. S Goodison, V Urquidi and D Tarin, CD44 cell adhesion molecules, *J. Clin. Pathol: Mol Pathol.*, 1999, 52, 189–196.
27. J Lesley, VC Hascall, M Tammi and R Hyman, Hyaluronan binding to cell surface CD44, *Journal of Biological Chemistry*, 2000, 275, 26967–26975.
28. JY Lee and AP Spicer, Hyaluronan: a multifunctional, megaDalton, stealth molecule, *Current Opinion in Cell Biology*, 2000, 12, 581–586.
29. E Sackman and RF Bruisma, Cell adhesion as wetting transition?, *ChemPhysChem*, 2002, 3, 262–269.
30. Y Cho and HY Choi. Opportunistic fungal infection among cancer patients. A ten year autopsy study. *Am. J. Clin. Pathol.* 1991, 72:617–621.
31. G. Reid. Probiotics for urogenital health. *Nutr Clin Care*, 2002, 5(1), 3–8.
32. YH An and RJ Friedman, Concise review of mechanisms of bacterial adhesion to biomaterial surfaces, *J. Biomed. Mater. Res. (Appl. Biomater.)*, 1998, 43, 338–348.
33. Schoor RA, Anderson B, Klumpp DJ, Schaeffer. Secretory IGA differentially promotes adherence of type 1-pilliated *Escherichia coli* to immortalized vaginal epithelial cell lines. Urology 2001; 57:556–561.

All publications and patents are incorporated by reference herein, as though individually incorporated by reference. The invention is not limited to the exact details shown and described, for it should be understood that many variations and modifications may be made while remaining within the spirit and scope of the invention.

What is claimed:

1. A method for preventing or treating a vaginal infection in a mammal consisting of administering to a mammalian vagina an effective amount of a hyaluronic acid compound or a hyaluronic acid compound that is mixed or covalently linked to a non-polysaccharide polymer, or a salt thereof, wherein the hyaluronic acid compound or hyaluronic acid compound that is mixed or covalently linked to a non-polysaccharide polymer, or salt thereof, can inhibit adherence of *Escherichia coli* or *Candida albicans* to mammalian epithelial cells.

2. The method of claim 1, wherein the hyaluronic acid compound or salt thereof prevents infection of pathogen in a mammalian vagina.

3. The method of claim 2, wherein the pathogen is a bacterial, fungal or trichomonial pathogen.

4. The method of claim 2, wherein the pathogen is *Candida albicans*.

5. The method of claim 2, wherein the pathogen is *Escherichia coli*.

6. The method of claim 1, wherein the hyaluronic acid compound or salt thereof comprises ($\beta$-1,4-)-linked D-glucuronic acid and ($\beta$1,3-)-N-acetyl-D-glucosamine.

7. The method of claim 1, wherein the hyaluronic acid compound or salt thereof comprises one or more glucose, glucuronic acid, mannose, mannuronic acid, galactose, galacturonic acid, gulose, guluronic acid, fucose, xylose, N-acetylneuraminic acid, or N-acetyl glucosamine saccharide units.

8. The method of claim 1, wherein the non-polysaccharide polymer is poly(ethylene glycol), poly(vinyl alcohol), poly (vinylpyrrolidone), or poly(2-hydroxylethyl methacrylate).

9. The method of claim 1, wherein the hyaluronic compound acid or salt thereof comprises a repeating disaccharide unit of formula I:

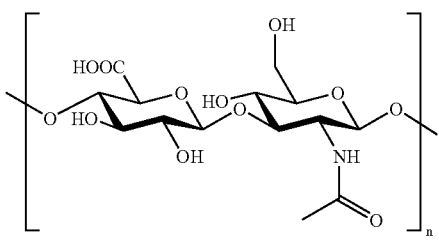

wherein n is an integer of about 2 to about 100,000.

10. The method of claim 9, wherein a lower alkyl replaces any of the hydrogen atoms from the hydroxy (—OH), carboxylic acid (—COOH) and methylenehydroxy (—CH$_2$—OH) substituents within one or more of the disaccharide units of formula I.

11. The method of claim 9, wherein an amino, a sulfate or a lower alkyl amino group replaces any of the OH groups from the hydroxy (—OH), carboxylic acid (—COOH) and methylenehydroxy (—CH$_2$—OH) substituents within one or more of the disaccharide units of formula I.

12. The method of claim 1, wherein the effective amount comprises about 0.01 milligrams to about 500 milligrams of hyaluronic acid compound or salt thereof.

* * * * *